United States Patent [19]

Hsu et al.

[11] Patent Number: 4,978,208

[45] Date of Patent: Dec. 18, 1990

[54] PHOTOELECTRONIC DIODE SPATIAL LIGHT MODULATOR AND EYE PROTECTION GOGGLES INCORPORATING THE SAME

[75] Inventors: Tsung-Yuan Hsu, Westlake Village; Shin-Tson Wu, Northridge; Robert Y. Loo, Los Angeles, all of Calif.

[73] Assignee: Hughes Aircraft Company, Los Angeles, Calif.

[21] Appl. No.: 383,698

[22] Filed: Jul. 24, 1989

[51] Int. Cl.$^5$ ............................ G02C 7/10; G02F 1/015
[52] U.S. Cl. ............................................ 351/45; 2/432; 340/760; 330/4.3; 350/353; 351/44
[58] Field of Search .................. 2/8, 432; 330/4.3; 340/760; 350/336, 342, 353, 354, 355, 356, 331 R, 448, 451, 452; 351/44, 45, 46; 362/800; 430/84, 95

[56] References Cited

U.S. PATENT DOCUMENTS 4,848,890 7/1989 Horn ...................................... 351/44
4,914,296 4/1990 Reinhold et al. .................... 250/330

OTHER PUBLICATIONS

W. P. Bleha, "Progress in Liquid Crystal Light Valves", *Laser Focus/Electro-Optics*, Oct. 1983, pp. 110–120.

Primary Examiner—Rodney B. Bovernick
Attorney, Agent, or Firm—V. D. Duraiswamy; P. M. Coble; W. K. Denson-Low

[57] ABSTRACT

A spatial light modulator includes a photosensor diode and a photoemitting diode array, each having two semiconductive layers of opposite electrical polarities, and which are sandwiched together with layers of the same polarity (P or N) in electrical contact with each other. Transparent electrode layers are formed on the opposite surfaces of the photosensor diode and photoemitting diode array respectively, in electrical contact with the layers of the opposite polarity. The individual photoemitting diodes are electrically and optically isolated from each other. With a voltage applied across the electrodes which causes the photosensor diode to be reverse biased and the photoemitting diodes to be forward biased, the photoemitting diode array generates a visual display which is a reproduction of a light image incident on the photosensor diode. The photosensor diode may be replaced by a single layer of a photoconductive material. Two of the spatial light modulators may be combined in a frame with suitable optics to provide eye protection goggles.

23 Claims, 4 Drawing Sheets

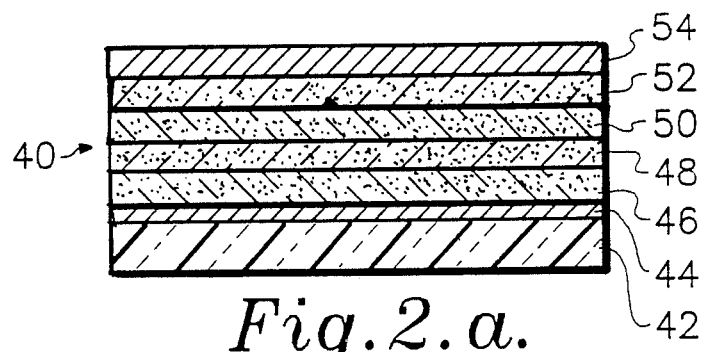
Fig.2.a.
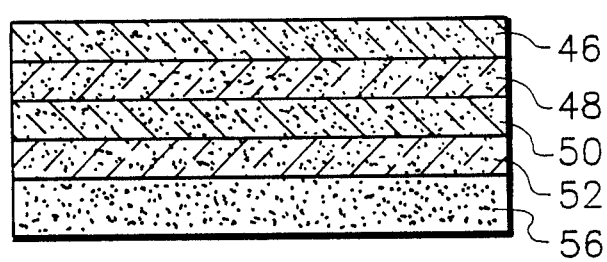
Fig.2.b.
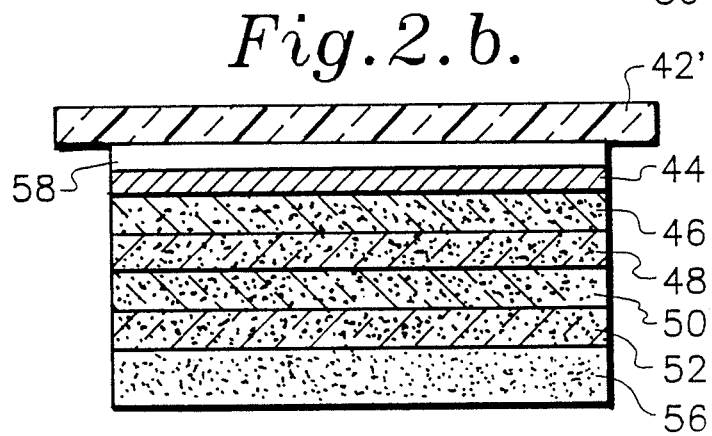
Fig.2.c
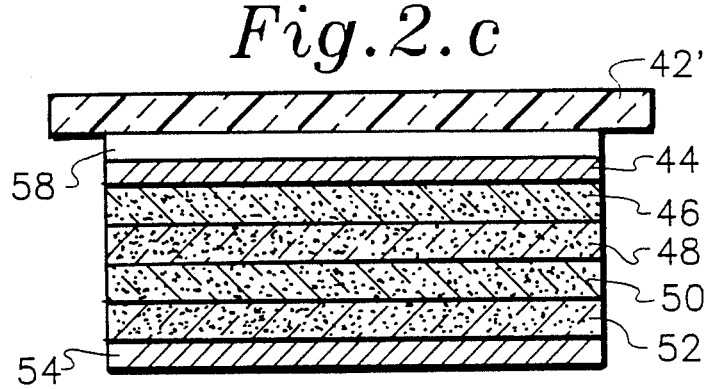
Fig.2.d.

ial light modulator including a photosensor diode and a photoemitting diode array which may be advantageously incorporated into a pair of eye protection goggles.

PHOTOELECTRONIC DIODE SPATIAL LIGHT MODULATOR AND EYE PROTECTION GOGGLES INCORPORATING THE SAME

BACKGROUND OF THE INVENTION

1. Field of the Invention

The present invention generally relates to the field of optoelectronics, and more specifically to a spatial light modulator including a photosensor diode and a photoemitting diode array which may be advantageously incorporated into a pair of eye protection goggles.

2. Description of the Related Art

Workers in scientific, technical, and construction environments are often exposed to hazards in the form of intense light from optical lasers, arc welding equipment, and other sources. A worker can easily suffer severe eye damage from intense light, especially if encountered without warning.

Conventional eye protection goggles or face plates consist merely of thick optical filters which absorb a large proportion of the light passing therethrough. A major disadvantage of this expedient is that the filters absorb so much light that a normally illuminated scene cannot be seen through them.

Spatial light modulators in the form of liquid crystal light valves (LCLV) are especially useful in large visual display applications. A LCLV is an optical-to-optical transducer that is capable of accepting a low-intensity visible light image and converting it, in real time, into an output image with light from another source. A general description of LCLV technology is presented in a paper entitled "Progress in Liquid Crystal Light Valves", by W. P. Bleha, Laser Focus/Electro-Optics, Oct. 1983, pp. 111-120.

Although advantageous in many applications, LCLVs require an external light source to produce the converted image, and are complex and expensive to manufacture on a commercial production basis. These factors preclude their use in eye protection goggles.

Night vision devices which utilize image intensifier tubes as their main active element are in widespread use. Although providing the desired visual image intensification, the tubes are delicate and sensitive. If a conventional night vision device were subjected to input light from an optical laser, the overload would be so severe that photosensitive coating in the tube would be damaged beyond repair and the device disabled.

SUMMARY OF THE INVENTION

A spatial light modulator embodying the present invention includes a flat, photosensor diode and a photoemitting diode array, each having two semiconductive layers of opposite electrical polarities, and which are sandwiched together with layers of the same polarity (P or N) in electrical contact with each other. Transparent electrode layers are formed on the opposite surfaces of the photosensor diode and photoemitting diode array respectively, in electrical contact with the layers of the opposite polarity. The individual photoemitting diodes are electrically and optically isolated from each other. With a voltage applied across the electrodes which causes the photosensor diode to be reverse biased and the photoemitting diodes to be forward biased, the photoemitting diode array generates a visual display which is a reproduction of a light image incident on the photosensor diode. The photosensor diode may be replaced by a photoconductive layer of, for example, cadmium sulfide.

The spatial light modulator of the invention is useful in applications requiring optical conversion of light, such as in optical data processing. Although it is within the scope of the invention to provide point or linear optical conversion, the present spatial light modulator is especially advantageous in the form of a flat, two dimensional array. The invention enables high speed operation in excess of 100 MHz, and high image contrast. It requires a low operating voltage and current, and can be solar powered in practical form. It does not require a polarizer or external readout light source. The damage threshold is very high, comparable to that of a LCLV. The present spatial light modulator can be manufactured as a large rectangular array at low cost on a commercial production basis using mature semiconductor mass production technology.

Two of the spatial light modulators may be combined in a frame with suitable optics to provide eye protection goggles. The present spatial light modulator is opaque to incident light, yet able to withstand high optical radiation intensities without damage or failure. As yet another application of the present invention, a spatial light modulator may be incorporated into the front end of a known night vision device, to provide protection for the image intensifier tube.

These and other features and advantages of the present invention will be apparent to those skilled in the art from the following detailed description, taken together with the accompanying drawings, in which like reference numerals refer to like parts.

DESCRIPTION OF THE DRAWINGS

FIGS. 2a to 2d are fragmentary sectional views illustrating the fabrication of a second spatial light modulator embodying the invention;

DETAILED DESCRIPTION OF THE INVENTION

Figure 1:
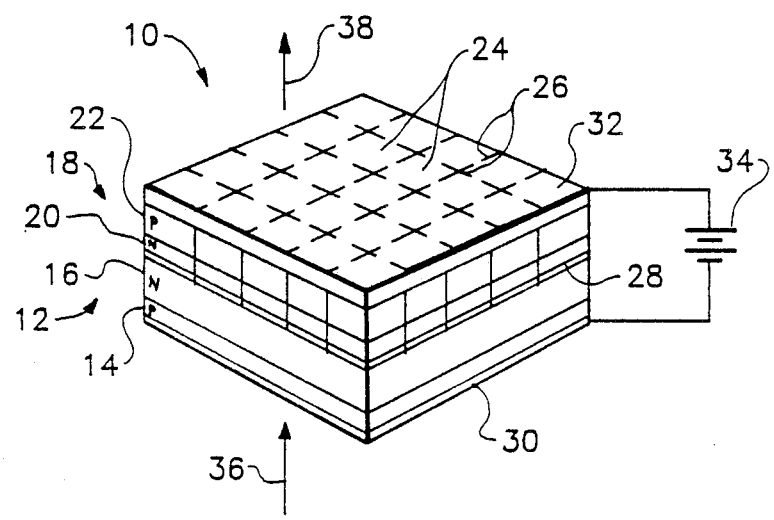
FIG. 1 is a sectioned perspective view of a spatial light modulator embodying the present invention.

Referring now to FIG. 1 of the drawing, a spatial light modulator 10 of the present invention is schematically illustrated. The modulator 10 is substantially in the form of a flat sheet or panel, but may have a degree of curvature which is suitable for the design of eyeglass or goggle lenses.

The modulator 10 includes a flat photosensor diode 12 having a P-doped layer 14 of positive electrical doping polarity and an N-doped layer 16 of negative electrical doping polarity. The layers 14 and 16 are in intimate electrical contact with each other to define a P-N diode junction (not designated) therebetween.

The modulator 10 further includes a flat photoemitting diode array 18 having an N-doped layer 20 and a P-doped layer 22 which define a P-N diode junction therebetween in a manner similar to the layers 14 and 16 of the photosensor diode 12. The layers 20 and 22 are divided into sections which constitute individual photoemitting diodes 24 by a rectangular grid of barriers 26 which electrically and optically isolate the photoemitting diodes 24 from each other. Although the layers 14 and 16 of the photosensor diode 12 are continuous, they are functionally divided into sections (not designated) which underlie the respective sections of the photoemitting diode array 18 constituting the individual photoemitting diodes 24. The N-doped regions of the layers 16 and 20, which have the same electrical doping polarity, are electrically connected together by means of a conductive adhesive 28 which is partitioned by the barriers 26 in the same configuration as the layers 20 and 22. In this manner, each photoemitting diode 24 is connected back-to-back with an underlying section of the photosensor diode 12 which functionally constitutes an individual photosensor diode (not designated).

The modulator 10 further includes transparent electrode layers 30 and 32 which are formed on and electrically connected to the layers 14 and 22 respectively to form a sandwich arrangement which also includes the layers 16, 20 and 28. Positive and negative terminals of an electrical power source 34, which may be a battery or solar cell, are connected to the electrodes 32 and 30, respectively. As a result, each photoemitting diode 24 and underlying respective section of the photosensor diode 12 is electrically connected in series, with the photoemitting diode 24 forward biased and the respective section of the photosensor diode 12 reverse biased.

The layers 14 and 16 of the photosensor diode 12 may be formed of any suitable material which has a large value of electrical resistance in the absence of incident light radiation, and which exhibit localized photoconduction to an increasing extent as the intensity of incident light radiation increases. Where the modulator 10 is to be utilized as an eyepiece element in a pair of eye protection goggles, the photosensor diode 12 may be formed of suitably doped layers of silicon or gallium arsenide (GaAs).

The layers 20 and 22 of the photoemitting diode array 18 may be formed of GaP, GaAlAs in the visible wavelength region, or any other suitable material which emits light having an intensity which increases as the value of electric current flowing therethrough increases. A preferred material for the layers 20 and 22 is suitably doped gallium-aluminum arsenide (GaAlAs), which emits red light. Generally, the photoemitting diodes 24 may be of any applicable type, such as light emitting diodes (LED) and laser diodes. A typical range of doping concentration for the photosensor diode layers and the photoemitting diode layers is $10^{17}$-$10^{18}$ atoms per cubic centimeter. The diodes can be homojunction or heterojunction structures.

The electrically conductive adhesive layer 28 may be formed of indium or conductive epoxy. The transparent electrodes 30 and 32 may be formed of indium tin oxide (ITO), AuGe, or AuTi, by way of example.

The barriers 26 may be in the form of grooves which provide an air gap between adjacent photoemitting diodes 24. Alternatively, the barriers 26 may be formed of electrically insulative regions formed in the layers 20, 22 and 28 by proton implantation or other suitable means.

Although the modulator 10 is schematically illustrated in FIG. 1 as consisting of a rectangular two-dimensional array having a small number of elements, the preferred form of the invention includes a large number of closely packed elements which provide a high value of optical resolution. However, the scope of the present invention further includes a linear array.

In operation, a light image is focussed by an optical system (not shown) onto the modulator 10 in the direction of an arrow 36. The image light passes through the transparent electrode 30 and impinges on the photosensor diode 12. The electrical resistance of the diode 12 decreases in a localized manner in proportion to the incident light intensity. Each photoemitting diode 24 emits light having an intensity which increases as the resistance of the respective series connected section of the photosensor diode 12 decreases. Thus, the photoemitting diode array 18 generates a light image through the transparent electrode 32 in the direction of an arrow 38 which is visible to an observer facing the array 18. The resolution of the display is equal to the number of elements in the array per unit of distance.

At least one of the layers 14, 16, 20, 22, and 28 is made optically opaque to prevent incident light from passing through the modulator 10. GaAs and GaAlAs, as well as silicon, are inherently opaque and provide the required function. At least the layer 14 of the modulator 10 is made of a material which is resistant to high levels of incident light intensity, thereby making the modulator 10 highly useful in applications where eye protection is desired.

Experiments have evidenced that an overall light conversion efficiency of 3% is easily attainable with a high contrast ratio, and 8% or more is possible using known optimized material systems. This is compatible with applications requiring eye protection in high light intensity environments, such as electrical arc welding. A high response or switching time on the order of 100 nanoseconds between emitting and non-emitting states has been observed. Although such fast response may not be required for eye protection goggles, it is desirable where the modulator 10 is used in optical data processing applications, in which the diode threshold inherent in the modulator may be utilized to eliminate noise in optical imaging logic gates. The converter 10 is further capable of wavelength conversion by making the photosensor diode 12 sensitive to light of a selected wavelength range and the photoemitting diode array 18 emit light of a different wavelength range.

The spatial light modulator 10 may be fabricated using a hybrid integration technique, with the photosensor 12 and photoemitting diode array 18 fabricated separately and joined together by means of the conductive adhesive 28. Various alternative embodiments of the present spatial light modulator fabricated by different techniques are illustrated in FIGS. 2a to 4.

In FIG. 2a, a modulator 40 includes a transparent substrate 42 of, for example, sapphire, on which is fabricated a transparent electrode layer 44, a P-doped photosensor layer 46, an N-doped photosensor layer 48, an N-doped photoemitting layer 50, a P-doped photoemitting layer 52 and a transparent electrode 54. It will be noted that the conductive adhesive layer 28 of the FIG. 1 embodiment is not required in the modulator 40 of FIG. 2a.

The process steps for fabricating the modulator 40 are illustrated in FIGS. 2b to 2d. In FIG. 2b, the photoemitting layers 52 and 50, made of a material such as GaAlAs, are deposited on a substrate 56 made of a lattice matched material such as GaAs. The photosensor layers 48 and 46 are formed on the layer 50.

In FIG. 2c, the transparent electrode layer 44, made of ITO or a gold alloy, is deposited on the layer 46. The sapphire substrate, which in this step of the process may be in the form of an oversize wafer or plate 42', is adhered to the electrode layer 44 by means of an ultraviolet curable cement 58.

In FIG. 2d, the GaAs substrate 56, which may be opaque in the visible wavelength region, is removed using selective chemical etching. The electrode layer 54, made of ITO or a gold alloy, is deposited on the etched surface of the photoemitting layer 52. Following the step of FIG. 2d, the substrate 42' is trimmed to constitute the substrate 42, and the finished modulator 40 has the configuration shown in FIG. 2a.

The component layers may be epitaxially grown using a monolithic integration technique such as liquid phase epitaxy, molecular beam epitaxy, or metal-organic chemical vapor deposition. Although advantageous for many applications, the selection of material systems for monolithic integration is somewhat limited due to the requirement of lattice matching.

Figure 3:
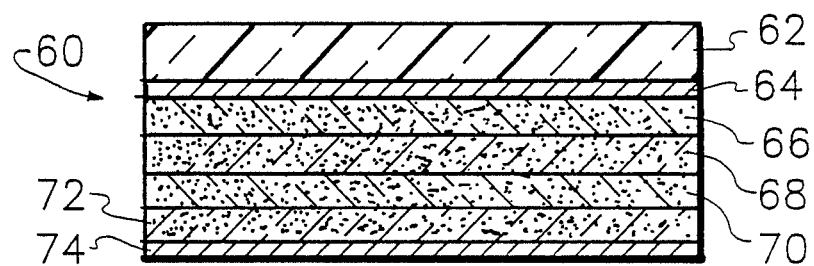
FIGS. 3 to 5 are fragmentary sectional views illustrating additional alternative embodiments of the present spatial light modulator.

FIG. 3 illustrates another modulator 60 of the invention which includes a transparent substrate 62 on which are epitaxially grown or otherwise formed a transparent electrode layer 64, a P-doped photoemitting layer 66, an N-doped photoemitting layer 68, an N-doped photosensor layer 70, a P-doped photosensor layer 72, and a transparent electrode layer 74.

Figure 4:
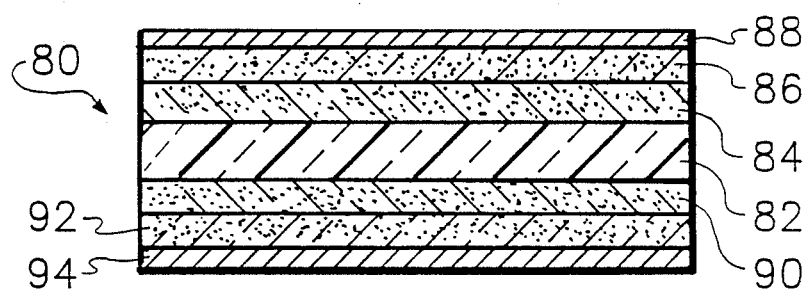

FIG. 4 illustrates another modulator 80 which includes a transparent or opaque substrate 82. An N-doped photoemitting layer 84, a P-doped photoemitting layer 86, and a transparent electrode layer 88 are formed on the upper surface of the substrate 82 in the middle of the structure. An N-doped photosensor layer 90, a P-doped photosensor layer 92 and a transparent electrode layer 94 are formed on the lower surface of the substrate 82. The substrate 82 must be formed of an electrically conductive material to interconnect the photosensor and photoemitting diodes, and be formed with barrier means (not shown) equivalent to the barrier means 26 illustrated in FIG. 1.

Figure 5:
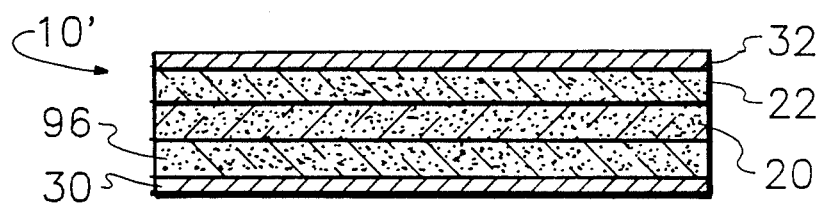

FIG. 5 illustrates yet another modulator embodying the present invention which is designated as 10', and differs from the modulator 10 in that the photosensor diode 12, which includes the layers 14 and 16, is replaced by a single photoconductive member in the form of a photoconductive layer 96. Thus, the electrical resistance of the layer 96 is inversely proportional to the intensity of incident light, providing the same action as the photosensor diode 12. The layer 96 acts as a dielectric material in the absence of light, and locally photoconducts in proportion to the intensity of light incident thereon. The layer 96 may be formed of any of a wide range of materials, including cadmium sulfide, silicon, germanium, gallium arsenide, or any other semiconductive material which exhibits photoconductivity. A further modification of the spatial light modulator 10' is that the conductive adhesive 28 has been omitted, and the layer 20 formed directly on the layer 96.

A spatial light modulator of the invention may be quite thin, with the operative component diode layers being approximately 10 micrometers thick in combination.

Figure 6:
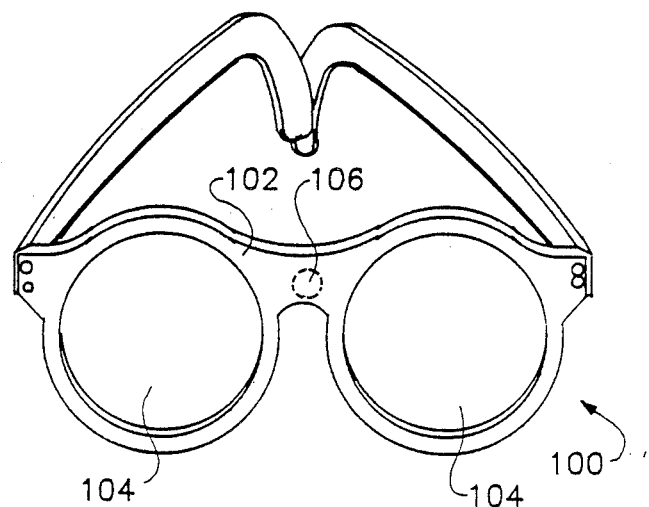
FIG. 6 is a perspective view illustrating a pair of eye protection goggles embodying the present invention.

A pair of eye protection goggles embodying the present invention is shown in FIG. 6 and generally designated as 100. The goggles 100 include a frame 102 and two eyepieces 104 which are supported by the frame 102. Further illustrated is a battery 106, which may be mounted at any desired location on or in the frame 102, for powering the eyepieces 104. Although the eye protection goggles 100 are illustrated as being of a conventional binocular configuration, it is within the scope of the present invention to provide an eye protection device in the form of a monocular or enlarged panel which is viewable with both eyes simultaneously.

Figure 7:
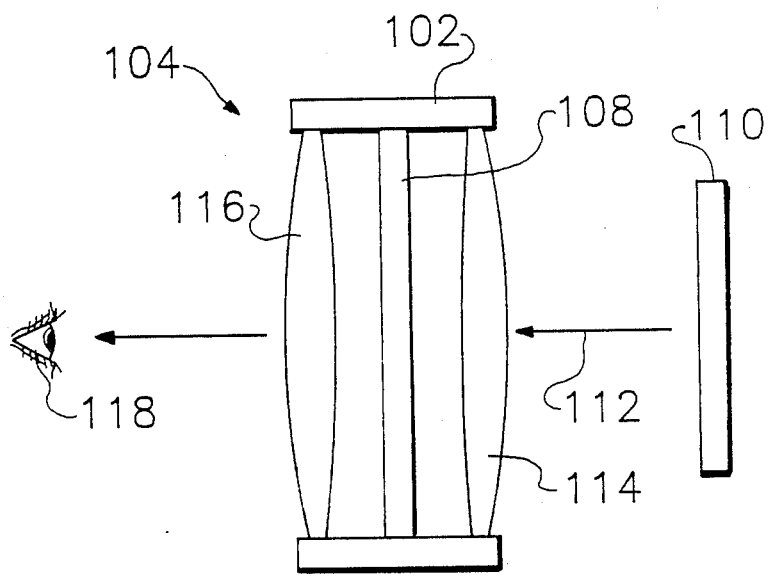
FIG. 7 is a sectional view of an eyepiece assembly of the eye protection goggles.

One of the eyepieces 104 is illustrated in FIG. 7, and includes a spatial light modulator 108 of the configuration illustrated in any of FIGS. 1 to 5. A light image of a scene 110 to be viewed is incident on the eyepiece 108 in the direction of an arrow 112 and focussed on the photosensor portion (not designated) of the modulator 108 by an optical objective lens 114, which may consist of multiple lens elements. An optical eyepiece lens 116 forms an image of the photoemitting diode portion (not designated) of the modulator 108 in the plane of a viewer's eye 118. Where the invention is embodied in the form of a large panel display which is viewable by both eyes of an observer, the eyepiece lens 116 may be omitted. It is further within the scope of the invention to replace the objective lens 114 with an optical fiber array, or any other means for focussing an image on the modulator 108.

Figure 8:
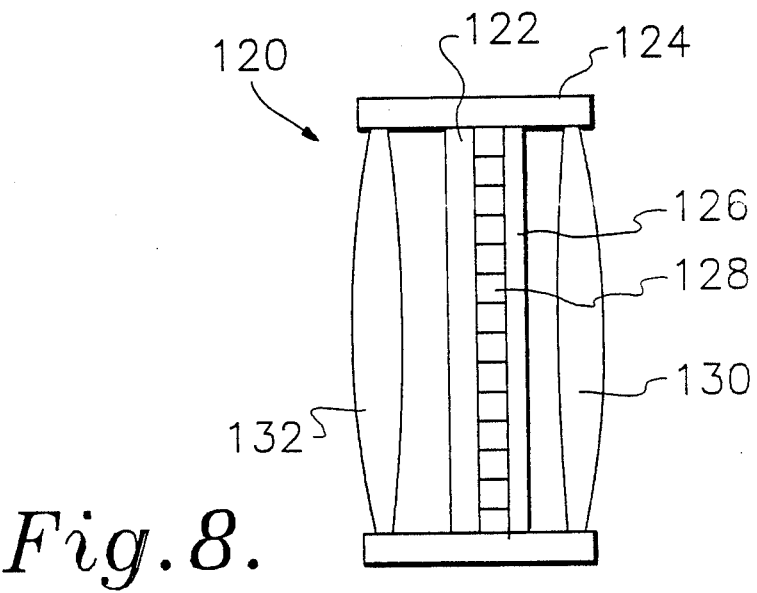
FIG. 8 is a sectional view illustrating a spatial light modulator of the invention incorporated into a front end of a night vision device.

FIG. 8 illustrates the present invention as incorporated into the front end of an eyepiece of a night vision device 120 for protection of a delicate and sensitive image intensification tube 122 thereof. A frame 124 supports the tube 122, as well as a spatial light modulator 126 of the invention and a fiber optic array 128 which couples a light image from the photoemitting diode section (not designated) of the modulator 126 to the image intensification tube 122. Further illustrated are an objective lens 130 and an eyepiece lens 132. The modulator 126 prevents the tube 122 from directly receiving light incident on the device 120 from the rightward direction, as viewed in the drawing, which may be of sufficient intensity to damage the tube 122.

While several illustrative embodiments of the invention have been shown and described, numerous variations and alternate embodiments will occur to those skilled in the art, without departing from the spirit and scope of the invention. For example, the relative polarities of the diode layers in the spatial light modulator may be reversed so that the P-doped regions, rather than the N-doped regions, are electrically connected together back-to-back at their common interface. Accordingly, it is intended that the present invention not be limited solely to the specifically described illustrative embodiments. Various modifications are contemplated and can be made without departing from the spirit and scope of the invention as defined by the appended claims.

We claim:

1. A spatial light modulator comprising:
   a photoconductive member;
   a photoemitting diode array including a plurality of photoemitting diodes which are electrically and optically isolated from each other and electrically connected to respective sections of the photoconductive member; and
   first and second transparent electrodes which sandwich the photoconductive member and photoemitting diode array therebetween and are electrically connected thereto respectively.

2. A spatial light modulator as in claim 1, in which the photoemitting diodes comprise light emitting diodes.

3. A spatial light modulator as in claim 1, in which the photoemitting diodes comprise laser diodes.

4. A spatial light modulator as in claim 1, further comprising an electrically conductive adhesive for adhering the photoconductive member and photoemitting diode array together and electrically interconnecting the respective sections of the photoconductive member and photoemitting diodes.

5. A spatial light modulator as in claim 1, further comprising a substrate for supporting the photoconductive member and photoemitting diode array, at least one of the substrate, photoconductive member and photoemitting diode array being optically opaque.

6. A spatial light modulator as in claim 1, in which the photoemitting diode array and respective sections of the photoconductive member are two dimensional.

7. A spatial light modulator as in claim 1, further comprising barrier means for electrically and optically isolating the photoemitting diodes from each other.

8. A spatial light modulator as in claim 7, in which the barrier means comprises grooves formed in the photoemitting diode array between adjacent photoemitting diodes.

9. A spatial light modulator as in claim 7, in which the barrier means comprises insulative regions formed in the photoemitting diode array between adjacent photoemitting diodes.

10. A spatial light modulator as in claim 7, in which the barrier means comprises insulative regions formed by proton implantation in the photoemitting diode array between adjacent photoemitting diodes.

11. A spatial light modulator as in claim 1, further comprising a substrate, the photoconductive member and photoemitting diode array being constituted by semiconductive layers formed on the substrate.

12. A spatial light modulator as in claim 1, further comprising optical means for forming a light image on the photoconductive member.

13. A spatial light modulator as in claim 1, further comprising optical means for forming a light image of the photoemitting diode array.

14. A spatial light modulator as in claim 1, further comprising power source means for applying an electrical potential across the first and second electrodes such that the photoemitting diodes are forward biased.

15. A spatial light modulator as in claim 1, in which the photoconductive member comprises a photosensor diode, the photoemitting diodes being electrically connected to the respective sections of the photosensor diode such that regions of the respective sections of the photosensor diode and photoemitting diodes having a first electrical polarity are connected together;
the first and second electrodes being electrically connected to regions of the photosensor diode and photoemitting diodes respectively having a second polarity which is opposite to the first polarity.

16. A spatial light modulator as in claim 15, further comprising power source means for applying an electrical potential across the first and second electrodes such that the photosensor diode is reverse biased and the photoemitting diodes are forward biased.

17. Eye protection goggles, including frame means, and at least one opaque eyepiece means supported by the frame means, each of said at least one eyepiece means comprising:
a photoconductive member;
a photoemitting diode array including a plurality of photoemitting diodes which are electrically and optically isolated from each other and electrically connected to respective sections of the photoconductive member; and
first and second transparent electrodes which sandwich the photoconductive member and photoemitting diode array therebetween and are electrically connected thereto respectively.

18. Eye protection goggles as in claim 17, further comprising power source means for applying an electrical potential across the first and second electrodes of said at least one eyepiece means such that the photoemitting diodes are forward biased.

19. Eye protection goggles as in claim 17, in which said at least one eyepiece means further comprises optical means for forming a light image on the photoconductive member.

20. Eye protection goggles as in claim 17, in which said at least one eyepiece means further comprises optical means for forming a light image of the photoemitting diode array.

21. Eye protection goggles as in claim 17, in which said at least one eyepiece means further comprises image intensification means for intensifying an image of the photoemitting diode array.

22. Eye protection goggles as in claim 17, in which photoconductive member of said at least one eyepiece means comprises a photosensor diode, the photoemitting diodes being electrically connected to the respective sections of the photosensor diode such that regions of the respective sections of the photosensor diode and photoemitting diodes having a first electrical polarity are connected together;
the first and second electrodes being electrically connected to regions of the photosensor diode and photoemitting diodes respectively having a second polarity which is opposite to the first polarity.

23. Eye protection goggles as in claim 22, further comprising power source means for applying an electrical potential across the first and second electrodes of said at least one eyepiece means such that the photosensor diode is reverse biased and the photoemitting diodes are forward biased.

* * * * *